United States Patent [19]

Muni et al.

[11] Patent Number: 5,316,706
[45] Date of Patent: May 31, 1994

[54] METHOD OF MANUFACTURING JOINTLESS CATHETER

[75] Inventors: Ketan P. Muni, San Jose; Michael S. Williams, Cupertino, both of Calif.

[73] Assignee: Advanced Cardiovascular Systems, Santa Clara, Calif.

[21] Appl. No.: 926,998

[22] Filed: Aug. 5, 1992

[51] Int. Cl.⁵ .................. B29C 35/12; B29C 47/88
[52] U.S. Cl. .............................. 264/25; 264/26; 264/209.1; 264/235; 264/346; 425/174.8 R
[58] Field of Search .......... 264/25, 26, 209.1, 209.7, 264/209.5, 209.3, 167, 149, 150, 235, 346, 237, 348; 425/380, 174.8 R

[56] References Cited

U.S. PATENT DOCUMENTS

| | | | |
|---|---|---|---|
| 3,752,617 | 8/1973 | Burlis et al. | 425/145 |
| 3,755,525 | 8/1973 | Sheridan et al. | 264/209.3 |
| 4,165,957 | 8/1979 | Kertscher | 264/174 |
| 4,216,253 | 8/1980 | Bonnebat et al. | 264/209.1 |
| 4,263,236 | 4/1981 | Briggs et al. | 264/26 |
| 4,276,250 | 6/1981 | Satchell et al. | 264/209.1 |
| 4,329,314 | 5/1982 | Jackson et al. | 264/519 |
| 4,385,635 | 5/1983 | Ruiz | 128/658 |
| 4,451,306 | 5/1984 | Verne | 264/210.1 |
| 4,963,306 | 10/1990 | Weldon | 264/149 |
| 5,059,375 | 10/1991 | Lindsay | 264/167 |

Primary Examiner—Jeffery Thurlow

[57] ABSTRACT

A catheter is formed from a single extrusion of cold crystallizable material in its amorphous state. Selected portions of the catheter are subsequently subjected to the material's cold crystallization temperatures for a selected period of time in order to transform those portions into a more crystalline form. Increased crystallinity profoundly affects the physical characteristics of the material. A jointless catheter having a relatively stiff body and a soft, pliable, and atraumatic tip is thereby provided.

6 Claims, 1 Drawing Sheet

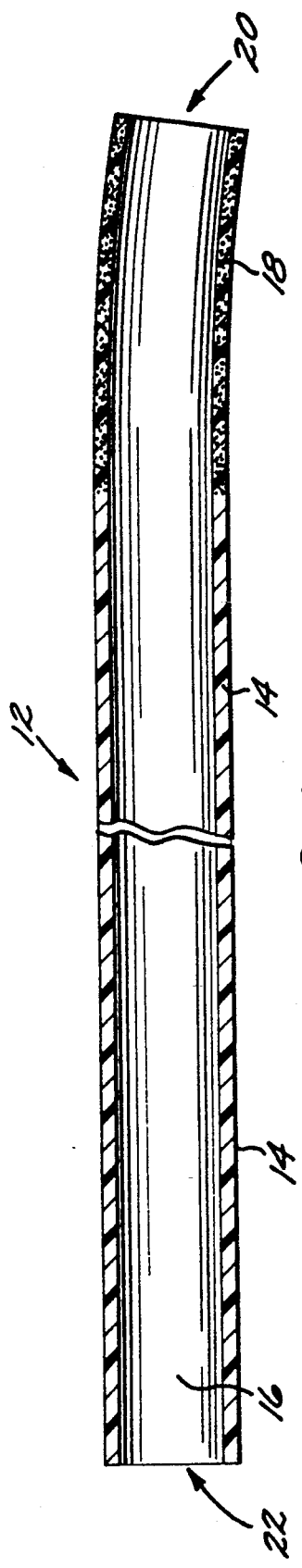
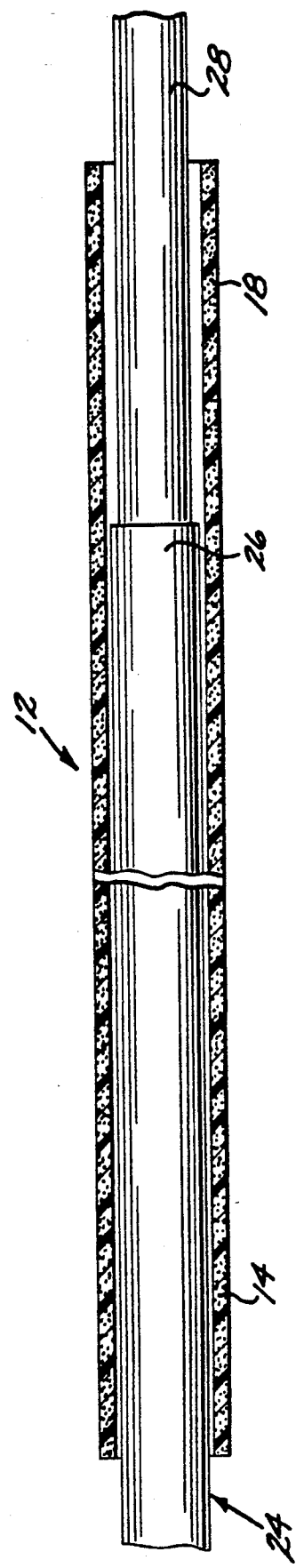

METHOD OF MANUFACTURING JOINTLESS CATHETER

BACKGROUND OF THE INVENTION

1. Field of the Invention

This invention relates generally to catheter-type devices used for various purposes including for example in the practice of angiography and angioplasty techniques. More specifically, the invention pertains to catheters and a method for producing catheters having fuseless and seamless structures that exhibit selectively varied physical characteristics along their lengths.

2. Brief Description of the Prior Art

Catheters used within a vascular system are required to have a number of apparently conflicting physical characteristics. For example, the catheter must be sufficiently rigid in the proximal region to enable its distal end to be maneuvered by manipulation of its proximal end. Both torsional as well as axial forces must therefore be transferable along the catheter's entire length despite the substantial frictional resistance that may be encountered. It is however simultaneously necessary for the catheter's distal end to be sufficiently soft so as not to traumatize the vascular walls when being advanced and sufficiently flexible to enable it to readily follow a potentially tortuous vascular path. Sufficient flexibility and an atraumatic tip are of similar importance in over-the-wire type applications wherein the catheter's leading edge may scrape against vessel walls as it is being advanced along a guide wire positioned in those vessels and wherein excessive rigidity would prevent the catheter from following a tightly curved wire. The catheter may further be limited with respect to its overall diameter in order to permit its introduction into small vessels yet may be called upon to handle substantial flow rates and pressures. In addition to variation in mechanical properties, certain applications may call for variation in the catheter's thermal, electrical, chemical, optical, and permeability properties at certain locations along its length. In all cases the catheter material must be non-toxic and should be non-thrombogenic, smooth-walled and resistant to kinking.

The design requirements set forth above have traditionally been approached with the use of multi-piece structures wherein for example a rather soft and flexible catheter tip is fused onto or otherwise attached to a relatively rigid, and high tensile strength catheter extrusion. Such designs are plagued by a number of inherent disadvantages including for example, the potentially compromised strength of the catheter at the junction between the tip and the catheter body which could result in a failure at that location. Additionally, since catheters are disposed of after a single use and cost is consequently of major concern, the production of at least two separate components and their required assembly can be economically prohibitive.

An alternative approach is exemplified by the catheter structure described in U.S. Pat. No. 4,385,635 to Ruiz. The required flexibility near the tip and the necessary rigidity in the rest of the catheter is achieved by a structure wherein a soft elastomeric sleeve encloses an inner reinforcing tube which tapers to zero wall thickness just short of the sleeve's end. The unreinforced sleeve end serves as the soft catheter tip while the necessary rigidity is imparted to the rest of the catheter by the presence of the reinforcing tube therein. Disadvantages associated with such a design include the substantial cost of manufacture and the fact that only a limited number of parameters would appear to be variable in this manner.

Weldon in U.S. Pat. No. 4,963,306 proposes a fuseless catheter structure wherein the desired variation of certain physical properties is achieved within a single extrusion. Partially polymerized material is extruded to form the catheter after which a selected portion thereof is induced to undergo solid state polymerization. Those portions that have undergone only a limited degree of polymerization remain flexible, while the further polymerization of other portions increases their strength and rigidity. A fuseless catheter appropriately treated retains a soft, flexible, and atraumatic tip while the remaining portion is rendered stiffer and stronger and is capable of withstanding higher internal pressures. It is stated that such catheter can be maneuvered through a circuitous vascular path without subjecting the vessel walls to trauma while radiopaque fluid can be delivered at higher flow rates with minimized danger of rupture. Weldon achieves solid state polymerization at selected portions of the catheter by subjecting those portions to a temperature above the boiling temperature of water and below the melting point of the extrudate while maintaining the balance of the catheter at substantially lower temperatures. It is conjectured that the removal of water from within the polymer network permits more complete polymerization to occur.

Disadvantages associated with the use of solid state polymerization techniques include the relatively modest enhancement of physical properties that is realizable, the relatively slow rate at which the cold polymerization reactions proceed, the relative difficulty involved in controlling the degree of polymerization achieved due to the exothermic nature of the reaction and although stiffness is increased, kink resistance, defined in terms of bend radius, is diminished.

SUMMARY OF THE INVENTION

The present invention overcomes the shortcomings of the prior art devices by providing a jointless and fuseless catheter wherein selected portions have an amorphous structure while other portions have a more crystalline structure. This variation in crystallinity imparts substantially varied physical properties to different portions of the same catheter, most notably providing for a substantial range in stiffness. The present invention further provides a method for producing such a catheter.

The catheter of the present invention is produced by first extruding a cold crystallizable material in its amorphous state. Selected portions of the extrudate are subsequently subjected to temperatures above the material's cold-crystallization temperature for a controlled period of time. It has been found that a 2%–50% crystallinity spread is attainable thereby which provides for a substantial variation in stiffness. Further advantages provided by the varied crystalline structure over a structure varyingly polymerized include enhancement of the material's kink resistance. While both increased crystallinity as well as increased polymerization result in a stiffer structure, the more highly crystallized material can be curved into a tighter radius without kinking. An increase in crystallinity additionally serves to increase thermal as well as electrical conductivity, enhances chemical resistance, reduces permeability to gasses, and results in diminished optical transmission.

By subjecting all but the distal end of a catheter extrusion to cold crystallization temperatures, a relatively stiff steerable and pushable catheter is provided having a substantially amorphous and hence soft, pliable and atraumatic tip. A further advantage afforded by employing cold crystallization techniques to produce a differentiated catheter structure is inherent in the controllability of the cold crystallization process. Additionally, an amorphous material is relatively easily extruded. By controlling temperature and time, a precise degree of crystallization can be achieved. The temperature of selected portions of the catheter can be raised by employing any of a variety of well known techniques; conduction as well as induction techniques are preferred.

Other features and advantages of the present invention will become apparent from the following detailed description, taken in conjunction with the accompanying drawings, which illustrates by way of example, the principles of the invention.

BRIEF DESCRIPTION OF THE DRAWINGS

FIG. 1 is an enlarged longitudinal cross-sectional view of a catheter according to the present invention; and FIG. 2 illustrates a catheter extrusion in the process of being transformed into the catheter illustrated in FIG. 1 according to the method of manufacture of the present invention.

DETAILED DESCRIPTION OF THE PREFERRED EMBODIMENT

FIG. 1 generally illustrates a catheter 12 according to the present invention. This particular illustration shows a single lumen structure 16 wherein the tip portion 18 is comprised of material in a generally flexible and amorphous state while the majority of its length, i.e., the catheter body 14, is comprised of the same material but in a substantially more crystalline form. Such catheter exhibits good pushability due to the catheter body's stiffness resulting from its relatively high crystallinity, and generally renders the catheter's distal end 20 readily maneuverable by manipulation of its proximal end 22. In addition to the increased stiffness, the enhanced crystallinity also serves to render the material more resistant to kinking. In other words, not only are greater forces required to constrain the material into a given radius of curvature, but smaller radii of curvature are attainable without causing the material to kink.

In addition to increased stiffness and kink resistance, the crystallized form of the catheter material additionally offers enhanced thermal and electrical conductance properties, increased resistance to chemicals and reduced permeability to gasses. The preferred application for the present invention is an angioplasty catheter. The differentiated properties may be advantageously exploited in a variety of catheter-type applications including, but not limited to introducers, balloon catheters, sheaths, and vascular as well as intravascular implants.

The present invention additionally provides for a method of producing a catheter as illustrated in FIG. 1. FIG. 2 illustrates a preferred method of cold crystallizing selected portions of an extruded tubular structure. Upon extrusion of the catheter 12 in its amorphous state, an inductance element 24, having a first section 26 subject to inductance heating and a second section 28 unresponsive thereto, is inserted into the catheter. The element is positioned such that the first section 26 is in contact with the body 14 of the catheter while the second section 28 extends through the portion of the catheter intended to function as its distal end 20. Heating is induced within section 26 so as to maintain a predetermined temperature for a predetermined period of time after which all heating is halted and element 24 is removed. Depending upon the material used, the required temperature can range form 80° C. to 250° C. and the required treatment time can vary from seconds to a few hours. Higher temperature results in a faster cold crystallization rate. Longer heating times result in increased crystallinity. The selective application of heat to the catheter results in the portion of the catheter adjacent the first section 26 transforming into a more crystalline state while the portion of the catheter adjacent the non-inducting section 28 remains substantially in its amorphous state. A catheter body 14 and catheter tip 18 is thereby formed. The present invention is not limited to a catheter having a relatively stiff body portion and a flexible distal end. The crystallinity of a device may be varied in any of a plurality of zones throughout its length. Isolated sections of the catheter can be subjected to elevated temperatures by any of a variety of other methods well known in the art. For example, a heating wire having zones of high resistance can be utilized in a fashion very similar to the above-described inductance-heating method. Alternative methods include utilization of radiated or convected energy.

The preferred thermoplastic material for practicing the present invention is either high or low molecular weight polyethylene terephthalate (PET). Cold crystallizable forms of polyester, copolyesters, polyamides, copolyamides, polyetheretherketone, polyolefins, polycarbonate, polyurethanes, and polyimides among others may also be employed. Cold crystallization temperatures for various materials are readily attainable from handbook-type sources such as *New Development in Polyesters derived from Terephthalic acid; A Polyetherester based on Polyethylene;* Author, A. B. Ijzermans; British Polymer Journal; 1975; Volume #7, pages 211–219.

EXAMPLE

Amorphous PET tubing with dimensions of 0.015 inches I.D. and 0.020 inches O.D. was extruded. The PET employed was Goodyear Traytuf 9506 having an intrinsic viscosity of 0.95 dl/g. A 100 cm portion was heated in a convection oven for 10 minutes at 125° C. In comparing some of the physical properties of the treated length of tubing to the same physical properties of untreated tubing, a 20–35% increase in crystallinity was noted having the effect of increasing the kink angle (as measured with a Tinius Olsen Stiffness Tester) from a 45–50° degree angle to 65–70° at an approximately 60% higher load.

While this example describes a certain material, dimensions, temperature, heating time, and heating method, it should be understood that they are not intended to be limiting. For example, as the composition or the dimensions of the tubing vary, the temperature and length of time for heating the tubing may also vary in order to achieve the novel characteristics of the invention.

While a particular form of the invention has been illustrated and described, it will also be apparent to those skilled in the art that various modifications can be made without departing from the spirit and scope of the invention. Accordingly, it is not intended that the invention be limited except as by the appended claims.

What is claimed is:

1. A method for forming a jointless catheter having differentiated physical characteristics along its length, comprising the steps of:
   selecting a cold-crystallizable thermoplastic material that is extrudable in its amorphous state;
   extruding said material in the form of said catheter; and
   causing selected portions of said catheter to undergo cold-crystallization whereby said portions that undergo cold-crystallization are rendered stiffer and more kink resistant and any portions not having undergone cold-crystallization remain relatively soft and pliable.

2. The method of claim 1 wherein said selected portions of said catheter are caused to undergo cold-crystallization with the application of heat thereto wherein a preselected temperature above said material's cold-crystallization temperature is maintained for a preselected period of time.

3. The method of claim 2 wherein said extruded material is polyethylene terephathalate and cold crystallization is achieved by maintaining said material at a temperature of from 110° C.–140° C. for a period of from 5 to 15 minutes.

4. The method of claim 2 wherein said extruded catheter has a proximal end and a distal end and wherein said preselected temperature is maintained in all but the distal end of said extrusion for said preselected period of time.

5. The method of claim 4 wherein said heat is applied via inductance heating.

6. The method of claim 5 wherein an inductance element is inserted into said catheter.

* * * * *